US011648419B2

(12) United States Patent
Li et al.

(10) Patent No.: US 11,648,419 B2
(45) Date of Patent: *May 16, 2023

(54) METHOD, APPARATUS, AND SYSTEM FOR SIMULATING A PARTICLE TRANSPORT AND DETERMINING HUMAN DOSE IN A RADIOTHERAPY

(71) Applicant: SHANGHAI UNITED IMAGING HEALTHCARE CO., LTD., Shanghai (CN)

(72) Inventors: Gui Li, Shanghai (CN); Yin Tang, Shanghai (CN); Shaoqiang Ye, Shanghai (CN); Juan Liu, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 309 days.

This patent is subject to a terminal disclaimer.

(21) Appl. No.: 16/989,820

(22) Filed: Aug. 10, 2020

(65) Prior Publication Data

US 2020/0368552 A1 Nov. 26, 2020

Related U.S. Application Data

(63) Continuation of application No. 15/563,576, filed as application No. PCT/CN2015/090289 on Sep. 22, 2015, now Pat. No. 10,737,115.

(30) Foreign Application Priority Data

Apr. 1, 2015 (CN) .......................... 201510152240.8

(51) Int. Cl.
*A61N 5/10* (2006.01)
*G16H 50/50* (2018.01)
*G16H 20/40* (2018.01)

(52) U.S. Cl.
CPC ........... *A61N 5/1031* (2013.01); *G16H 20/40* (2018.01); *G16H 50/50* (2018.01); *A61N 5/1042* (2013.01); *A61N 2005/1034* (2013.01)

(58) Field of Classification Search
CPC ................ A61N 5/1031; A61N 5/1042; A61N 2005/1034; G16H 20/40; G16H 50/50; G06F 19/00
See application file for complete search history.

(56) References Cited

U.S. PATENT DOCUMENTS

2006/0285640 A1* 12/2006 Nizin ...................... G06F 30/00
378/65
2013/0121469 A1 5/2013 Sobering et al.
(Continued)

FOREIGN PATENT DOCUMENTS

CN 102201036 A 9/2011
CN 103065056 A 4/2013
(Continued)

OTHER PUBLICATIONS

Romano, Paul Koilath. Parallel Algorithms for Monte Carlo Particle Transport Simulation on Exascale Computing Architectures. Diss. Massachusetts Institute of Technology, 2013. 199 Pages. (Year: 2013).*

(Continued)

*Primary Examiner* — Eunhee Kim
(74) *Attorney, Agent, or Firm* — Metis IP LLC

(57) ABSTRACT

A method for simulating a particle transport may include recording transport paths of inputted particles and determining an uncertainty of each of lattice cells based on the transport paths of each batch of the inputted particles, a lattice cell being a qualified lattice cell if an uncertainty of the lattice cell does not exceed a first threshold; determining a standard-reaching rate of lattice cells in a region of interest (ROI), the ROI including at least one lattice cell, the (Continued)

standard-reaching rate of lattice cells in the ROI being equal to a ratio of the number of qualified lattice cells to a total number of lattice cells in the ROI; and if the standard-reaching rate of lattice cells in the ROI exceeds a second threshold, stopping inputting particles, and outputting the transport paths of the inputted particles.

20 Claims, 4 Drawing Sheets

(56) References Cited

U.S. PATENT DOCUMENTS

| | | |
|---|---|---|
| 2015/0154374 A1 | 6/2015 | Hissoiny |
| 2015/0213630 A1* | 7/2015 | Szirmay-Kalos ......... G06T 1/20 382/131 |
| 2018/0085599 A1 | 3/2018 | Li et al. |

FOREIGN PATENT DOCUMENTS

| | | | |
|---|---|---|---|
| CN | 104361215 A | 2/2015 | |
| CN | 104376217 A | 2/2015 | |
| CN | 104407374 A | 3/2015 | |
| WO | WO-0040298 A1 * | 7/2000 | ........... A61N 5/1031 |
| WO | WO-0145556 A1 * | 6/2001 | ........... A61N 5/1031 |
| WO | WO-2012032609 A1 * | 3/2012 | ........... A61N 5/1031 |
| WO | 2013049839 A2 | 4/2013 | |

OTHER PUBLICATIONS

Paganetti, Harald. "Range uncertainties in proton therapy and the role of Monte Carlo simulations." Physics in Medicine & Biology 57.11 (2012): p. R99-R117. (Year: 2012).*
First Office Action in Chinese Application No. 201510152240.8 dated Mar. 2, 2017, 11 pages.
International Search Report in PCT/CN2015/090289 dated Dec. 31, 2015, 5 pages.
Written Opinion in PCT/CN2015/090289 dated Dec. 31, 2015, 11 pages.

* cited by examiner

METHOD, APPARATUS, AND SYSTEM FOR SIMULATING A PARTICLE TRANSPORT AND DETERMINING HUMAN DOSE IN A RADIOTHERAPY

CROSS-REFERENCE TO RELATED APPLICATIONS

This application is a continuation of U.S. application Ser. No. 15/563,576, filed on Sep. 30, 2017, now U.S. Pat. No. 10,737,115, issued on Aug. 11, 2020, which is a national phase entry of International Application No. PCT/CN2015/090289, filed on Sep. 22, 2015, which claims priority of Chinese Patent Application No. 201510152240.8, filed on Apr. 1, 2015. Each of the above-referenced applications is expressly incorporated herein by reference to their entireties.

TECHNICAL FIELD

The present disclosure relates to radiotherapy techniques, and more particularly, methods and apparatuses for simulating a particle transport, methods for determining a human dose in a radiotherapy, and systems for radiotherapy.

BACKGROUND

In the field of radiotherapy technique, methods for determining a dose distribution in a human tissue may broadly include two categories, including a semi-empirical analytic method and a Monte Carlo method.

The semi-empirical analytic method may include a method based on an off-axis ratio (OAR) empirical equation, a convolution/superposition method based on a pencil beam kernel and a point kernel, etc. However, the semi-empirical analytic method may have a limited accuracy.

The Monte Carlo method may be not substituted due to a capability of solving complex problems (e.g., complex geometry, a complex arrangement of a radiation source, etc.). The Monte Carlo method may be used to establish models relating to a physical process accurately with less approximation in a radiotherapy. The biggest disadvantage of the Monte Carlo method may be its large computational strength and time-consuming.

SUMMARY

The present disclosure may be used to solve how to improve a simulation efficiency of a particle transport in a radiotherapy.

To solve the above technical problem, a method for simulating a particle transport is provided. The method may be used to simulate an energy distribution of particles in a lattice cell. The method may include:

estimating a total number of incident particles required, generating incident particles, and inputting particles in batches;

recording transport paths of inputted particles;

determining an uncertainty of each of lattice cells based on the transport paths of each batch of the inputted particles, a lattice cell being a qualified lattice cell if an uncertainty of the lattice cell does not exceed a first threshold;

determining a standard-reaching rate of lattice cells in a region of interest (ROI), the ROI including at least one lattice cell, the standard-reaching rate of lattice cells in the ROI being equal to a ratio of the number of qualified lattice cells to a total number of lattice cells in the ROI;

if the standard-reaching rate of lattice cells in the ROI exceeds a second threshold, stopping inputting particles, and outputting the transport paths of the inputted particles, or if the standard-reaching rate of lattice cells in the ROI does not exceed the second threshold, continuing inputting particles until the number of inputted incident particles reaches the total number of incident particles required.

In some embodiments, incident particles belonging to a same batch may have a similar energy, or a same type, or a similar energy as well as a same type.

In some embodiments, the inputting particles in batches may include:

inputting particles in batches according to different types of incident particles.

In some embodiments, the transport paths of the inputted particles may include energy information relating to incident particles, speed information relating to incident particles, and other path information relating to incident particles, the speed information relating to incident particles including an incident direction of an incident particle, and the recording transport paths of the inputted particles may include:

designating a recorded transport path of a recorded particle as a transport path of an incident particle if energy information and incident direction information of the recorded particle are close to those of the incident particle.

In some embodiments, the other path information relating to incident particles may include type information relating to incident particles, incident position information relating to incident particles, weight information relating to incident particles, and information relating to lattice cells that the inputted particles pass;

the information relating to lattice cells that the inputted particles pass may include energy distributions and uncertainties corresponding to lattice cells that the inputted particles pass.

In some embodiments, the method may further include: when a batch of particles are inputted:

if a particle enters a second importance lattice cell from a first importance lattice cell, splitting, according to a first probability, the particle in the batch of particles. Particles generated by the particle splitting may have a decreased weight such that a total weight of the batch of particles remains unchanged. An importance level of the first importance lattice cell may be lower than that of the second importance lattice cell;

if a particle enters a fourth importance lattice cell from a third importance lattice cell, eliminating, according to a second probability, the particle in the batch of particles. The particle not being eliminated may have an increased weight such that the total weight of the batch of particles remains unchanged. An importance level of the third importance lattice cell may be higher than that of the fourth importance lattice cell.

In some embodiments, the first probability may be equal to a ratio of the importance level of the first importance lattice cell to the importance level of the second importance lattice cell, and the second probability may be equal to a ratio of the importance level of the fourth importance lattice cell and the importance level of the third importance lattice cell.

In some embodiments, an importance level of an importance lattice cell may be set manually, or automatically according to information relating to the importance lattice cell. The information relating to the importance lattice cell may include an uncertainty or a physical property of the importance lattice cell.

In some embodiments, the method may further include:

performing a dynamic denoising operation on an uncertainty of a dose distribution relating to incident particles based on historical transport paths of inputted particles.

In some embodiments, the performing dynamic denoising operation on an uncertainty of a dose distribution relating to incident particles based on the transport paths of the inputted particles may include:

determining a three-dimensional dose distribution of particles in a lattice cell and an uncertainty corresponding to the three-dimensional dose distribution of particles;

performing a filtering operation on the three-dimensional dose distribution such that the filtered three-dimensional dose distribution is continuously derivative in three dimensions; and determining an uncertainty corresponding to the filtered three-dimensional dose distribution.

In some embodiments, the method may further include: importing a geometrical model, the geometrical model including a lattice cell relating to a simulated object, a physical material, a weight of the lattice cell and/or a geometrical virtual section. The geometrical virtual section may be used to define the physical material corresponding to the lattice cell to make the simulated object corresponding to the lattice cell including a homogenized material. The transport paths of the inputted particles may relate to the geometrical virtual section.

To solve the above technical problem, a method for determining a human dose in a radiotherapy is provided. The method may include: determining a human dose in a radiotherapy based on an energy distribution of particles in a lattice cell determined according to the method for simulating a particle transport as described above.

To solve the above technical problem, a particle transport simulation apparatus is provided. The apparatus may be used to simulate an energy distribution of particles in a lattice cell. The apparatus may include: a source processing module, a transport processing module, a noise processing module, and an outputting module;

the source processing module may be configured to estimate a total number of incident particles required, generate incident particles, and input particles in batches;

the transport processing module may be configured to record transport paths of inputted particles;

the noise processing module may be configured to:

determining an uncertainty of each of lattice cells based on the transport paths of each batch of the inputted particles, a lattice cell being a qualified lattice cell if an uncertainty of the lattice cell does not exceed a first threshold;

determining a standard-reaching rate of lattice cells in a region of interest (ROI), the ROI including at least one lattice cell, the standard-reaching rate of lattice cells in the ROI being equal to a ratio of the number of qualified lattice cells to a total number of lattice cells in the ROI; and if the standard-reaching rate of lattice cells in the ROI exceeds a second threshold, stopping inputting particles, and outputting the transport paths of the inputted particles, or if the standard-reaching rate of lattice cells in the ROI does not exceed the second threshold, continuing inputting particles until the number of inputted particles reaches the total number of incident particles required.

To solve the above technical problem, a system for radiotherapy is provided. The system may include:

a particle transport simulation apparatus as described above, the particle transport simulation apparatus being configured to simulate an energy distribution of particles in a lattice cell;

a dose determination apparatus being configured to determine a human dose in a radiotherapy based on the energy distribution of particles in the lattice cell determined by the particle transport simulation apparatus.

Beneficial effects of the present disclosure may include:

the present disclosure may estimate a total number of incident particles required, and estimate a total number of particles required to be transported in a specific phantom based on a user's requirements for uncertainty, which may be designated as a total computation target. Thus, unnecessary particle transports may be reduced when a user's target is reached. The number of transported particles may be reduced to improve a simulation efficiency in some cases that the particle transport simulation cannot be truncated.

According to the present disclosure, the speed of simulating a particle transport may be improved. A computation target may be quickly reached by processing and evaluating an uncertainty of particles being transported, and the particle transport simulation may be truncated after reaching the computation target. Thereby the user's requirements for uncertainty may be satisfied meanwhile the computation time is decreased and the simulation efficiency is improved greatly.

According to the present disclosure, the number of sampled particles in regions of interest (ROIs) may be dynamically adjusted according to the uncertainty of particles being transported, and particles may be transported in batches under the premise of ensuring an overall uncertainty balance. Thus, the number of sampled particles and unnecessary particle transports may be reduced to save a large amount of computation time.

According to some embodiments of the present disclosure, incident particles may be classified and processed separately using a particle assimilation parallel processing technique. The incident particles may be classified according to energy and type of incident particles. Incident particles having a similar energy and a same type may be classified into a same batch, such that parallel computing units may complete computation in close time, thereby the simulation speed of parallel computing may be increased.

According to some embodiments of the present disclosure, a dynamic denoising may be achieved by performing a filtering operation on a dose distribution and uncertainties of particles after a simulation of each batch of particles. The balance of uncertainties may be improved, and the uncertainties relating to computing points of all ROIs may be decreased to an acceptable range.

According to some embodiments of the present disclosure, the homogeneity of incident particles may also be increased. Directions of incident particles may be homogenized to decrease uncertainties of source incident particles which may facilitate the particle dynamic denoising.

According to some embodiments of the present disclosure, virtual collision reactions (virtual reactions) and real physical reactions (real reactions) may be sampled distinctively in the simulation of a particle transport. Transport degrees of particles may be sampled, and directions and energies of particles may be not sampled under the virtual reactions. Directions and energies of particles may be re-sampled only under the real reactions. Thereby, the number of sampled particles may be reduced. According to the present disclosure, the number of sampled particles may be reduced by applying the following operations, including: reducing the number of sampled energies and directions for a virtual section in a particle transport; copying a path of a same incident particle directly to avoid repeated sampling; truncating particles based on energy to reduce transports of low-energy particles; and truncating particles based on weight to reduce transports of low importance particles.

DETAILED DESCRIPTION

Figure 1:
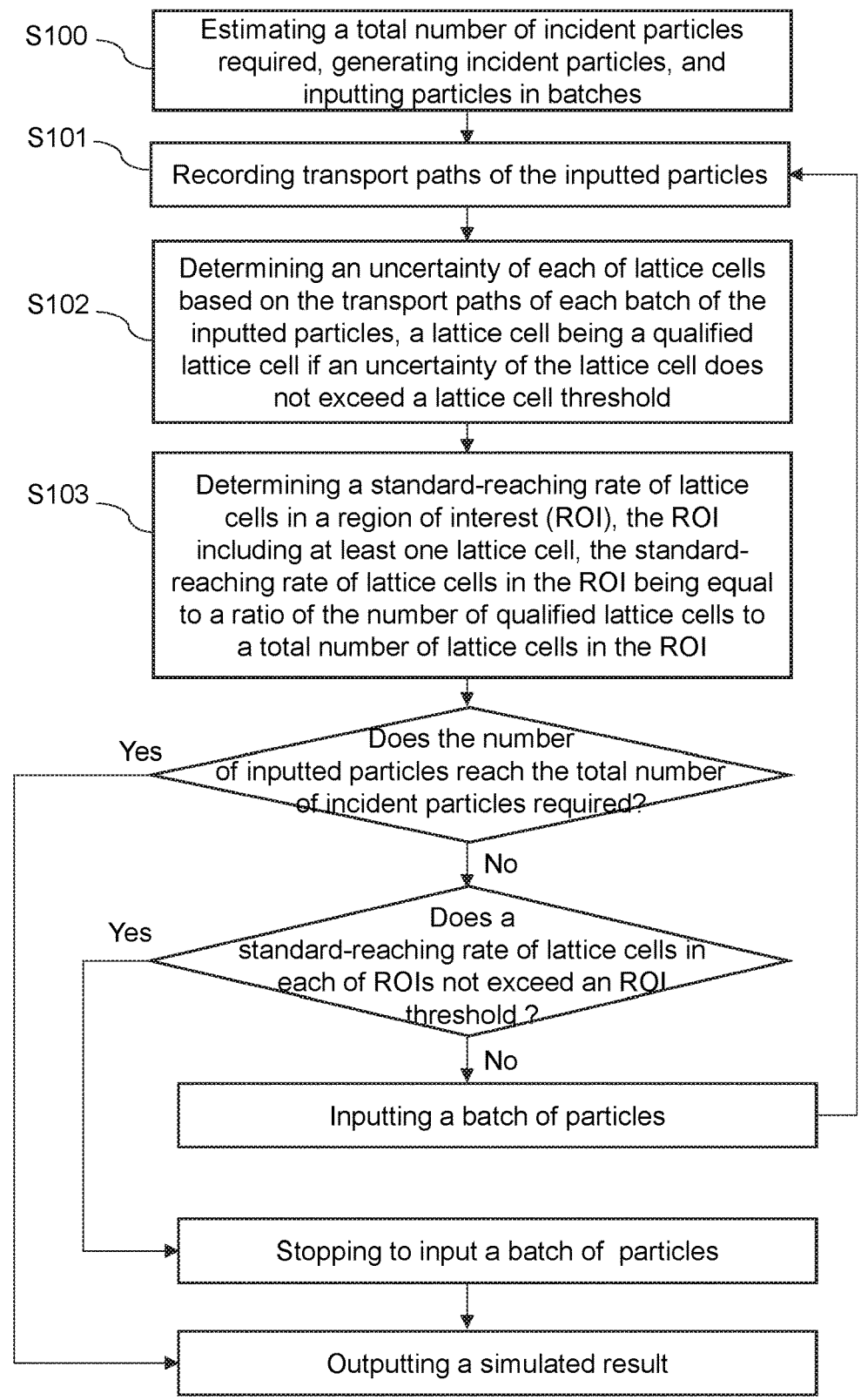
FIG. 1 is a flowchart illustrating an exemplary process for simulating a particle transport according to some embodiments of the present disclosure.

In the field of radiotherapy, ray beams generated by various types of therapy machine may need to be simulated, such as high-energy electron beams generated by an accelerator, proton beams, heavy ion and photon beams, cobalt-60 (Co) photon beams, and X-ray beams generated by an X-ray therapy apparatus. Ray beams generated by a simulation therapy apparatus may mainly output simulation information of particles, and record information relating to particles arriving at or passing through a geometrical space defined by a user. The information relating to particles may include charge carried by a particle, energy, a position, a direction of a particle, and course marks relating to materials a particle passing through.

A method for simulating a particle transport based on the Monte Carlo method may need to input information relating to characteristics of therapy beams, such as an energy spectrum distribution, angular distribution, spatial distribution, etc., of particles in an incident field. According to the inputted information, transports of a large number of particles may be simulated based on Monte Carlo method.

A method for simulating particle transport using the Monte Carlo method may be used to simulate a therapy head of an accelerator. The method may include:

firstly, establishing a user application for simulating a therapy head of an accelerator and sectional data relating to required particles interacting with a medium;

secondly, completing an input of a user, mainly including a geometrical definition relating to a component and module in the therapy head of the accelerator, a definition relating to incident particle beams, and a selection of control parameters relating to the user application;

then, performing a simulation computing and analyzing a computing result, and inputting the computing result as a source item for determining an absorbed dose of a phantom.

A particle simulation using the Monte Carlo algorithm may be accurate by applying a random sampling method. However, it is generally known that sampling characteristics of the Monte Carlo method may make it consume time inherently, and a simulation accuracy may be improved by a large number of random number samplings.

According to some embodiments of the present disclosure, a method for simulating a particle transport using the Monte Carlo method may reduce particle samplings by an algorithm combining a particle number estimation with a particle uncertainty, thus, greatly improving the speed and efficiency of simulating a particle transport based on the Monte Carlo method.

In order to make purposes, features and effects of the present disclosure more apparent and easier to understand, exemplary embodiments of the present disclosure may be described in detail with reference to the drawings.

In the following detailed description, numerous specific details are set forth by way of examples in order to provide a thorough understanding of the relevant disclosure, but the present disclosure may be implemented otherwise than as described herein, thus the present disclosure is not limited to the embodiments disclosed below.

Embodiment 1

A particle transport simulation using a Monte Carlo algorithm may achieve an accurate computing by using a large number of random sampling. Particularly, in order to satisfy a user's requirement for an uncertainty of a particle transport, it may need to simulate a large number of particles, which may consume time.

According to an embodiment of the present disclosure, a method for simulating a particle transport is provided. The method may be used to simulate an energy distribution of particles in a lattice cell. The particle samplings and computing time may be reduced by determining an uncertainty of a geometrical lattice cell, distinguishing an importance level of a lattice cell, and balancing uncertainties of lattice cells in an ROI based on the Monte Carlo algorithm.

As shown in FIG. 1, the method for simulating a particle transport may include:

in step S100, a total number of incident particles required may be estimated, incident particles may be generated, and particles may be inputted in batches.

The incident particles may be generated based on a source, and the source may be a simulation result of a known radiation source using a Monte Carlo tool. The source may have a form of a phase space source based on a phase space file.

The estimation of the number of incident particles may include determining a relationship between a particle number and an uncertainty by pre-simulating different numbers of particles in a homogenized phantom (e.g., a water phantom), a simulated human body, or a reference human body, and determining a mapping relationship between the particle number and the uncertainty by an interpolating or fitting operation, and determining an estimation result. The estimation result may be a total number of incident particles in a particle transport simulation.

The inputted particles may be generated based on different types of sources, such as a source of a photon type, a source of an electron type, or a source of a proton type. In the present embodiment, a method for inputting particles may include:

classifying incident particles having the same type, a similar energy, or a similar energy as well as the same type, into the same category, and processing particles of the same category in batches based on each category of incident particles;

inputting, based on a category and batch of incident particles, particles alternately in batches according to a distribution of sources generating the incident particles.

For example, mixed sources of a photon type and an electron-type may be described as an example. The mixed sources may be divided into M batches. Each batch may have photons and electrons. A ratio of photons to electrons in each batch may be constant. All batches may be transported until a computing relating to all the batches is completed. Each batch of the same type may also be divided into N sub-batches according to energy.

In the present embodiment, incident particles may be classified according to energy and type. Particles having a similar energy as well as the same type may be designated as a same sub-batch such that the waiting time between multiple threads in a parallel computing may be reduced, thereby increasing a simulation speed of the parallel computing.

In the present embodiment, different types of particles may be transported according to a distribution of sources, such that an uncertainty of the simulation computing may be reduced, and an error introduced may be decreased while the speed of the parallel computing is improved.

In some embodiments, the inputting method described above may be adaptively modified, such as only designating particles having a similar energy as well as a same type as a same batch and inputting particles in batches directly; or inputting particles generated by different sources directly and alternately, or inputting a part of particles directly, or inputting a part of particles after being optimized according to the present embodiment above, all of which may be implemented.

Referring back to FIG. 1, the method for simulating a particle transport in this embodiment may further include:

In step S101, transport paths of inputted particles may be recorded.

Transport information of particles may be sampled according to reaction type characteristics of different particles in a particle transport simulation using the Monte Carlo method. As used herein, transport information being sampled relating to a particle may be referred to as a transport path. The transport path may be a set of information describing a sampled physical reaction type of the particle. A basic physical parameter and a model relating to a sampled physical reaction type of a particle may be pre-stored in a Monte Carlo tool. Hence, a basic physical parameter and a model may be obtained according to a type of a particle, an energy of a particle, a speed of a particle, a property of a material corresponding to the position of a particle located, such that a transport path of a particle may be determined.

The basic physical parameter above may include a differential scattering section of a physical reaction, an average free path of a physical reaction, etc., and the model may include a photoelectric effect, a Compton scattering, a pair reaction, etc., for describing a photon.

In the present embodiment, the transport path may include all information relating to a sampled physical reaction type of a particle, such as: a basic physical parameter and a model of the sampled physical reaction type, energy information of an incident particle, speed information of an incident particle, and other path information of an incident particle. The speed information of an incident particle may include an incident direction of the incident particle. The other path information of an incident particle may include type information of an incident particle, incident position information of an incident particle, weight information of an incident particle, information of lattice cells that an inputted particle pass, and uncertainties corresponding to lattice cells that the inputted particle pass.

Step S101 of the present embodiment for recording transport paths of inputted particles may include sampling particles and storing the transport paths of inputted particles based on sampled particles. When a particle is sampled, a basic physical parameter and a model relating to a physical reaction type may be sampled. The recording of the transport paths may also be simplified in the present embodiment when the information above is determined, including:

designating a recorded transport path of a recorded particle as a transport path of an incident particle if energy information and incident direction information of the recorded particle are close to those of the incident particle.

In some other embodiments, a sampling result relating to a basic physical parameter and a model of a physical reaction type and a recorded transport path of a recorded particle may be copied and designated as a transport path of an incident particle according to energy information and incident direction information of an inputted particle are close to those of a recorded particle.

The simplified recording method in the present embodiment may copy a repeated path of a particle based on same incident particles (the same incident particles may refer to particles having similar energy information and incident direction) to avoid repeated sampling, reduce the sampling number of overall particles, and improve a simulation efficiency of a Monte Carlo tool.

For a particle not copying a transport path directly, a sampling of the incident particle and a storage of a transport path of the incident particle may include determining information relating to a sampled physical reaction described above based on a random number. The information relating to the sampled physical reaction may be used to simulate a particle transport based on the Monte Carlo method to generate a transport path of the incident particle.

Based on the prior art, it may be known that a particle transport simulation based on the Monte Carlo method needs to simulate a large number of particles to satisfy a requirement for uncertainty. Thus, the simulation algorithm may consume much time. Referring back to FIG. 1, the present embodiment may reduce the number of sampled particles based on a global uncertainty to ensure an equalization of the global uncertainty according to following operations including:

in step S102, an uncertainty of each of lattice cells may be determined based on the transport paths of each batch of the inputted particles. A lattice cell may be a qualified lattice cell if an uncertainty of the lattice cell does not exceed a lattice cell threshold;

in step S103, a standard-reaching rate of lattice cells in a region of interest (ROI) may be determined. The ROI may include at least one lattice cell. The standard-reaching rate of lattice cells in the ROI may be equal to a ratio of the number of qualified lattice cells to a total number of lattice cells in the ROI.

The lattice cell threshold may be used to evaluate the standard-reaching rate of a lattice cell, such that the standard-reaching rate of the lattice cell may satisfy a predetermined requirement.

Steps S102 and S103 may be performed, after each batch of incident particles have been sampled and transport paths of each batch of incident particles have been stored. An uncertainty of a lattice cell may be used to evaluate an uncertainty of a geometric lattice cell that undergoes a section reaction with particles. As a particle transport simulation based on the Monte Carlo method may have different requirements for uncertainties, an evaluation of a standard-reaching rate in ROIs may be used to balance the above uncertainties based on a balance of a standard-reaching rate of each of the ROIs.

If a standard-reaching rate of lattice cells in an ROI exceeds a preset threshold (the preset threshold may be referred to as an ROI threshold in FIG. 1), the standard-reaching rate of lattice cells in the ROI may be evaluated to satisfy the predetermined requirement. Then, the Monte Carlo simulation may be truncated, also referred to as stopping inputting particles, and a local simulation result (including the recorded transport paths of the recorded particles) may be outputted. The above uncertainty evaluation of the ROI may balance the global uncertainty and reduce unnecessary particle samplings and transports under satisfying a requirement for the global uncertainty, which may save much time and greatly improve a Monte Carlo simulation efficiency.

In addition, the present embodiment may also relate to a determination of an uncertainty of a lattice cell. The evaluation of an uncertainty of a lattice cell may have multiple definitions based on different uncertainty criteria. The present embodiment discloses the following two evaluation ways for reference.

An evaluation way may include:

determining sectional data relating to an interaction between a particle and each lattice cell based on transport paths of each batch of inputted particles, the sectional data including an actual probability that the particles undergo a reaction in the lattice cell;

comparing the actual probability that the particles undergo the reaction in the lattice cell with an expected probability that the particles undergo the reaction to obtain an uncertainty of the lattice cell.

The uncertainty evaluation of the lattice cell described above may take a section reaction relating to particles as the standard. It is known from the prior art that the section reaction relating to particles may refer to a probability that a particle reacts with a section of a lattice cell. The reaction may include that energy of a particle is absorbed by a lattice cell the particle passing. The reaction may be different as different absorption capabilities of lattice cells. According to different particle reactions, an expected probability that a particle undergoes a reaction and an actual probability that the particle undergoes the reaction in a lattice cell may be compared to determine an uncertainty of a probability that the reaction happens (such as the difference between the expected probability and the actual probability). An uncertainty of the lattice cell may be obtained based on an evaluation function relating to an uncertainty of probabilities that multiple reactions happen in the lattice cell. The evaluation function may include a sum function, a mean function, etc.

Another evaluation way may include:

determining a particle number density in a lattice cell based on transport paths of each batch of inputted particles;

determining a distribution curve of a particle number density in a relevant lattice cell according to the lattice cell and a sequence relating to the particle number density; and determining an uncertainty of the lattice cell based on the distribution curve.

The uncertainty evaluation of a lattice cell described above may take a particle number density of the lattice cell as a standard. The particle number density of a lattice cell may refer to the number of incident particles passing through the lattice cell. After a batch of inputted particles finish to be transported, the particle number density in a lattice cell may be determined based on transport paths of the batch of inputted particles, and a corresponding relationship between a lattice cell and a particle number density may be determined (a string of discrete sequences denoted by two-dimensional coordinates). A distribution curve of particle number densities relating to lattice cells may be fitted and determined based on the corresponding relationship. A difference of a particle number density relating to a lattice cell may be determined by comparing a value of the particle number density relating to the lattice cell on the determined distribution curve with a particle number density of the lattice cell in an actual transport, thereby an uncertainty of the lattice cell may be determined.

If a standard-reaching rate of lattice cells in each of ROIs does not satisfy the preset threshold, the next batch of incident particles may be continued to be generated and inputted, and steps S101 to S103 may be repeated until a standard-reaching rate of lattice cells in each of ROIs satisfies the preset threshold, or the number of inputted particles reaches the estimated total number of incident particles. Then, a local simulation result (including all recorded transport paths of recorded particles) may also be outputted.

Embodiment 2

Figure 2:
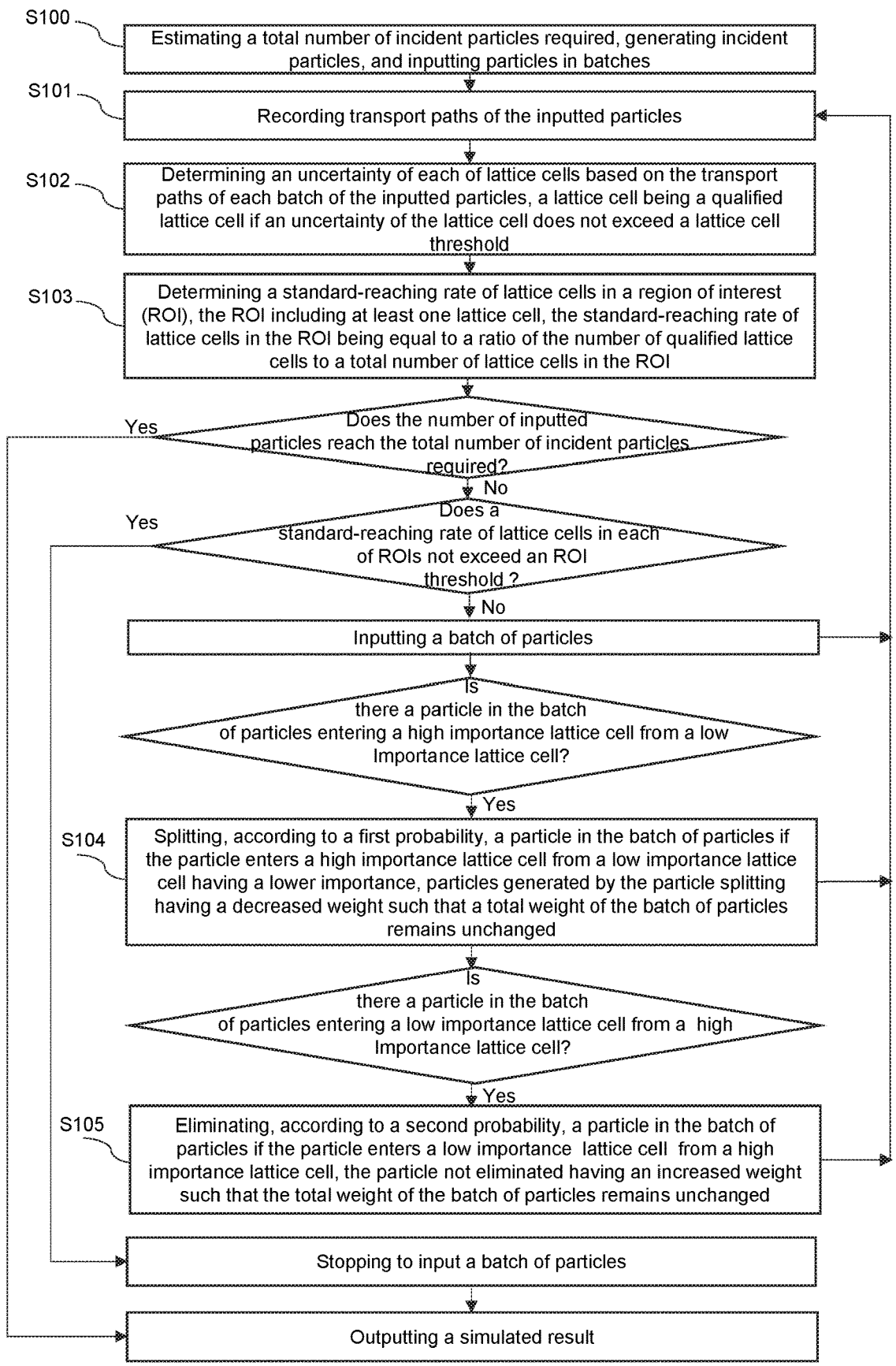
FIG. 2 is a flowchart illustrating another exemplary process for simulating a particle transport according to some embodiments of the present disclosure.

The present embodiment provides a method as shown in FIG. 2 for simulating a particle transport based on the first embodiment, which may be used to balance uncertainties according to a global uncertainty of a simulation. The sampling number of particles may be adjusted dynamically according to a distribution of the uncertainties. The method may include:

steps S100 to S103, which may be performed according to Embodiment 1.

When a batch of incident particles are inputted, an inputted particle may be processed as follows based on a transport process of incident particles:

in step S104, if the transport process of incident particles shows a particle in the batch of particles entering a high importance lattice cell from a low importance lattice cell, the particle entering the high importance lattice cell may be split according to a first probability. Transport paths of particles generated by the particle splitting may copy that of the particle before splitting, and weights of the particles generated by the particle splitting may be decreased such that a total weight of the batch of particles remains unchanged.

in step S105, if the transport process of incident particles shows a particle in the batch of particles entering a low importance lattice cell from a high importance lattice cell, the particle entering the low importance lattice cell may be eliminated according to a second probability. A transport path of the particle not eliminated may be unchanged, and a weight of the particle not eliminated may be increased such that the total weight of the batch of particles remains unchanged.

For simplicity, in step S104 of FIG. 2, the low importance lattice cell may be defined as a first importance lattice cell, and the high importance lattice cell may be defined as a second importance lattice cell; in step S105, the high importance lattice cell may be defined as a third importance lattice cell, and the low importance lattice cell may be defined as a fourth importance lattice cell. However, it should be appreciated that importance lattice cells from the first importance lattice cell to the fourth importance lattice cell may be not necessarily different importance lattice cells, which are only relative concepts to distinguish importance levels of the lattice cells. Importance level scopes of the importance lattice cells from the first importance lattice cell to the fourth importance lattice cell may overlap.

An importance lattice cell and an importance level of the importance lattice cell may be set manually, or automatically according to information relating to the importance lattice cell. The information relating to the importance lattice cell may include an uncertainty or a physical property of the importance lattice cell.

In some embodiments, an importance lattice cell and an importance level of the importance lattice cell may be preset manually before a radiotherapy by an operator via using an application software of a radiotherapy system. For example, several regions that may have a tumor in an ROI may be set as importance lattice cells, and importance levels (e.g., specific values) of the importance lattice cells may be set respectively.

An importance level of an importance lattice cell may also be set automatically according to an uncertainty of a lattice cell. In general, the higher an uncertainty of a lattice cell is, the higher an importance level of the lattice cell may be.

In steps S104 and S105, the first probability may be equal to a ratio of the importance level of the first importance lattice cell to the importance level of the second importance lattice cell, and the second probability may be equal to a ratio of the importance level of the fourth importance lattice cell to the importance level of the third importance lattice cell.

In the present embodiment, a particle entering a high importance lattice cell from a low importance lattice cell may be split according to the first probability that may increase the number of transported particles dynamically, and decrease an uncertainty of a lattice cell with a higher importance level, such that the simulation accuracy of a particle transport may be improved. The method as described above may balance an uncertainty of each of the ROIs in the first embodiment, such that batches of particle transports may be reduced and the simulation efficiency may be improved. A particle entering a low importance lattice cell from a high importance lattice cell may be split according to the second probability which may decrease the number of transported particles dynamically on the premise of ensuring the simulation accuracy and further improve the simulation efficiency.

Embodiment 3

Figure 3:
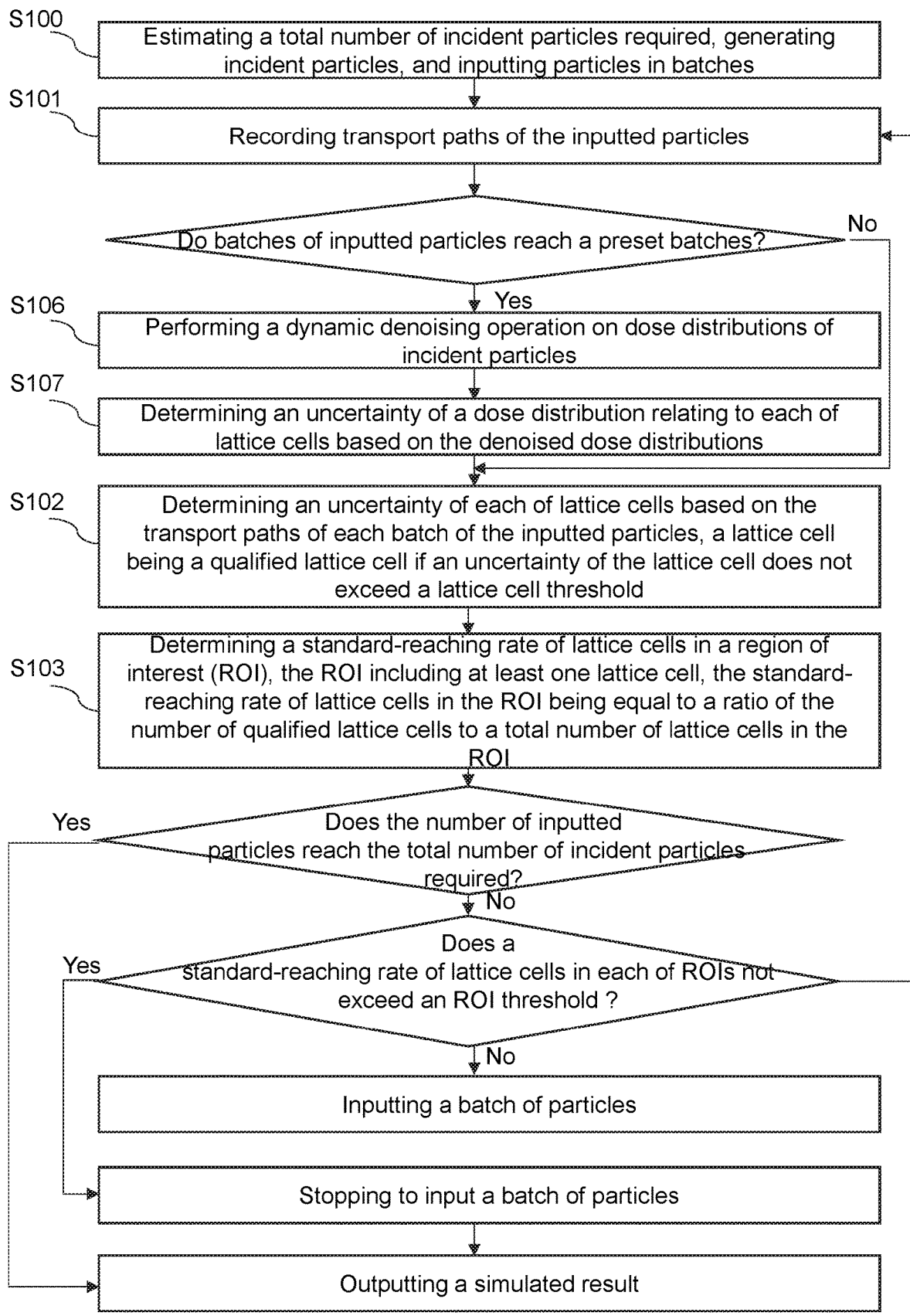
FIG. 3 is a flowchart illustrating another exemplary process for simulating a particle transport according to some embodiments of the present disclosure.

The present embodiment provides a method for simulating particle transport as shown in FIG. 3 based on the first embodiment. After simulating transport paths of predetermined batches of particles, a global uncertainty may be denoised dynamically based on historical transport paths of inputted particles according to input particles in batches, thereby reducing uncertainty in the particle transport simulation, which may help to reduce the sampling number of particles and improve the simulation efficiency. The method may include the following steps:

steps S100 to S103, which may be performed according to Embodiment 1.

In the particle transport simulation, if the batch number of inputted particle reaches a predetermined number, the following steps may be performed:

in step S106, a dynamic denoising operation may be performed on a dose distribution relating to incident particles.

In the present embodiment, the dynamic denoising operation may include:

determining a three-dimensional curve of a dose distribution of particles in a lattice cell (also referred to as a three-dimensional dose distribution of particles in a lattice cell) and an uncertainty corresponding to the dose distribution. The dose distribution of particles in the lattice cell may be determined an energy distribution of particles obtained based on a simulation, specifically, an energy distribution of particles with unit mass.

performing a filtering operation on the three-dimensional curve such that the filtered three-dimensional curve is continuously derivative in three dimensions;

determining an uncertainty corresponding to the filtered dose distribution.

In step S107, the uncertainty of the dose distribution in each lattice cell determined based on the dynamic denoising operation may be outputted.

In some embodiments, the uncertainty of the dose distribution in each lattice cell may be determined based on the three-dimensional curve of the dose distribution processed based on the filtering operation.

The filtering operation may eliminate noises such as burr on the three-dimensional curve of the dose distribution, and smooth the three-dimensional curve. Then an uncertainty of a dose distribution of particles in a lattice cell may be determined according to the smoothed three-dimensional curve, which may denoising the particle transport simulation integrally and may be helpful for a next particle transport simulation.

Embodiment 4

The present embodiment provides a method for simulating a particle transport, which defines a geometrical model relating to a simulation object (the simulation object may include a variety of therapy apparatuses in the field of radiotherapy, such as an accelerator therapy head) in a simulation process. The present embodiment may include:

importing a geometrical model, and other simulation steps. The other simulation steps may include any one of steps as described in Embodiment 1, Embodiment 2, and Embodiment 3.

The geometrical model may include a lattice cell relating to a simulated object, a physical material, a weight of the lattice cell and/or a geometrical virtual section. The geometrical virtual section may be used to define the physical material corresponding to the lattice cell to make the simulated object corresponding to the lattice cell including a homogenized material. The transport paths of the inputted particles may relate to the geometrical virtual section.

The present embodiment may relate to a geometrical virtual section. The geometrical virtual section may be a sampling probability that a particle undergoes a section reaction including a real reaction and a virtual reaction. For a transport of a particle, the geometric virtual section may be defined as $\Sigma_{max}$, in one sampling, the probability that the particle undergoes a real reaction may be $\Sigma_r$, and the probability that the particle undergoes a virtual reaction may be $\Sigma_r'$, r=1~R; wherein, r is a natural number representing sampling times of the particle, R is a natural number greater than or equal to 1 representing the specific number that the particle is sampled in limited times; and the geometric virtual section $\Sigma_{max}$ may satisfy following conditions:

$$\Sigma_{max} = \max(\Sigma_1, \Sigma_2, \ldots, \Sigma_{R-1}, \Sigma_R);$$

$$\Sigma_{max} = \Sigma_1 + \Sigma_1' = \Sigma_2 + \Sigma_2' = \ldots = \Sigma_R + \Sigma_R';$$

A sampling probability of a section reaction may be a maximum probability that a particle passes a lattice cell after the particle being sampled in limited times according to the conditions above. When the conditions are satisfied, all materials may use a geometric virtual section $\Sigma_{max}$ for performing transport length samplings under a particle transport simulation on the whole model. The probability that each material undergoes a real reaction is $\Sigma_r/\Sigma_{max}$, and the probability that each material undergoes a virtual reaction is $\Sigma_r'/\Sigma_{max}$. Thus, a high consistency with a real physical transport may be maintained when using a virtual section transport.

Figure 4:
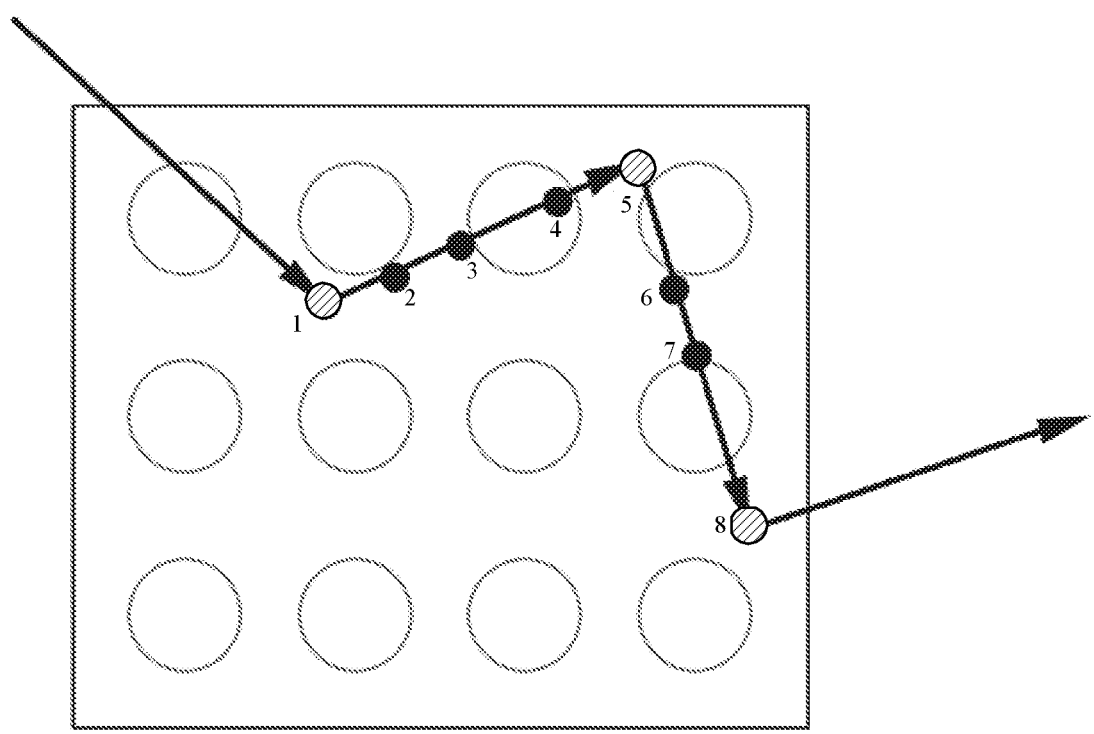
FIG. 4 is a schematic diagram illustrating a section reaction of particles in a particle transport according to some embodiments of the present disclosure.

Referring to FIG. 4, FIG. 4 is a schematic diagram of a section reaction in a particle transport. The arrow direction is an incident direction of a particle. A white circle represents a geometrical lattice cell. A black circle represents a position where a particle undergoes a virtual reaction (virtual collision), and a shadow circle represents a position where a particle undergoes a real reaction (real physical reaction, such as a photoelectric effect and a Compton effect). The transport path of the particle is 1-2-3-4-5-6-7-8, wherein, 1, 5, 8 represent positions of the real reaction, and 2, 3, 4, 6, 7 represent positions of the virtual reaction. It may be seen that after the virtual collision reaction happens, only re-samplings relating to the transport degree are needed, re-samplings relating to the particle direction and energy are not needed, and only in the real reaction, re-samplings relating to the particle direction and energy are needed.

Thus, the geometric virtual section in the present embodiment is different from that in the prior art, which is defined by ways as follows:

a particle may be sampled according to a sampling probability of the section reaction to pass through the lattice cell;

the sampling probability of the section reaction may be the sum of a sampling probability of the real reaction and a sampling probability of the virtual reaction;

a sampling when the particle happens the real reaction with the lattice cell may include a sampling relating to a transport degree, a direction and an energy, while a sampling when the particle happens the virtual reaction with the lattice cell may only include a sampling relating to transport degree.

Embodiment 5

The present embodiment provides a method for determining a human dose in a radiotherapy, including:

simulating a particle transport to obtain an energy distribution of particles in a lattice cell; and determining a human dose in a radiotherapy based on the energy distribution of particles in the lattice cell, wherein, the particle transport may be simulated according to any one of the embodiments 1 to 4.

Embodiment 6

The present embodiment provides an apparatus for simulating a particle transport corresponding to Embodiment 1. The apparatus may be used to simulate an energy distribution of particles in a lattice cell, including a source processing module, a transport processing module, a noise processing module, and an outputting module.

The source processing module may be configured to perform step S100.

The transport processing module may be configured to perform step S101.

The noise processing module may be configured to perform steps S102 and S103, and a local simulation result may be outputted by the outputting module.

In other embodiments, the apparatus for simulating a particle transport may also correspond to Embodiment 2. The difference from the present embodiment is that the noise processing module may be configured to perform steps S104 and S105.

In other embodiments, the apparatus for simulating a particle transport may also correspond to Embodiment 3. The difference from the present embodiment is that the noise processing module may be configured to perform steps S106 and S107.

Embodiment 7

The present embodiment provides an apparatus for simulating a particle transport corresponding to the fourth embodiment. The apparatus may be configured to simulate an energy distribution of particles in a lattice cell, comprising: a source processing module, a transport processing module, a noise processing module, an outputting module, an inputting module and a geometrical processing module.

The source processing module may be configured to perform step S100.

The transport processing module may be configured to perform step S101.

The noise processing module may be configured to perform steps S102 and S103, and the outputting module may output a local simulation result;

The inputting module may be configured to import a geometrical model as described in Embodiment 4 to the geometrical processing module.

Embodiment 8

The present embodiment provides a radiotherapy system, including:

a particle transport simulation apparatus being configured to simulate an energy distribution of particles in a lattice cell as described in connection with the Embodiment 6 and Embodiment 7; and a dose determination apparatus being configured to determine a human dose in a radiotherapy based on the energy distribution of particles in the lattice cell determined by the particle transport simulation apparatus.

Although the present disclosure has been described above in preferred embodiments, they are not intended to limit the disclosure, and without departing from the spirit and scope of the disclosure, any skilled in the art may use the methods and technical contents disclosed above to make a possible change and modification. Therefore, for contents without departing from the technical solution of the present disclosure, any of simple modifications, equal variations and modifications made to the above embodiments according to the technical spirit of the present disclosure are within the scope of the technical scope of the present disclosure.

We claim:

1. A method for simulating a particle transport, the method comprising:

obtaining transport paths of at least a portion of simulated particles;

determining, based on the transport paths, an uncertainty of each of lattice cells in each of multiple regions of interest (ROIs), the uncertainty indicating whether a simulated particle undergoes a reaction in each of the lattice cells;

determining an evaluation result associated with the particle transport by evaluating, based on the uncertainty of each of the lattice cells, the particle transport in the lattice cells: and adjusting, based on the evaluation result, the particle transport to equalize global uncertainties of the multiple ROIs such that the global uncertainty of each of the multiple ROIs corresponding to the adjusted particle transport does not exceed a threshold.

2. The method of claim 1, wherein
the evaluation result associated with the lattice cells indicates whether a standard-reaching rate of the lattice cells in each of the multiple ROIs exceeds a second threshold, and
the determining an evaluation result includes:
for each of the multiple ROIs, determining, based on the uncertainty of each of the lattice cells in the ROI, the standard-reaching rate of the lattice cells in the ROI, the standard-reaching rate of lattice cells in the ROI being equal to a ratio of a count of qualified lattice cells in the ROI to a total count of the lattice cells in the ROI, the uncertainty of each of the qualified lattice cells in the ROI not exceeding a third threshold.

3. The method of claim 2, wherein the determining, based on the uncertainty of each of the lattice cells in the ROI, the standard-reaching rate of the lattice cells in the ROI includes:
determining, based on the uncertainty of each of the lattice cells in the ROI and the first threshold, the count of qualified lattice cells in the ROI; and
determining, based on the count of qualified lattice cells in the ROI, the standard-reaching rate of the lattice cells in the ROI.

4. The method of claim 2, wherein the third threshold is determined based on the standard-reaching rate of the lattice cells in the ROI such that the standard-reaching rate of the lattice cells in the ROI exceeds a fourth threshold.

5. The method of claim 2, wherein the adjusting, based on the evaluation result, the particle transport includes:
in response to determining that the standard-reaching rate of lattice cells in the ROI exceeds the second threshold, stopping the particle transport; and
outputting the transport paths of the at least a portion of simulated particles.

6. The method of claim 2, wherein the adjusting, based on the evaluation result, the particle transport includes:
in response to determining that the standard-reaching rate of lattice cells in the ROI does not exceeds the second threshold, continuing to perform the particle transport until the standard-reaching rate of lattice cells in the ROI exceeds the second threshold.

7. The method of claim 1, wherein the evaluation result associated with the lattice cells indicates whether each of the at least a portion of simulated particles enters a second lattice cell with a second level from a first lattice cell with a first level, the first level being lower than the second level, and the determining an evaluation result includes:
for each of the multiple ROIs,
determining, based on the uncertainty of each of the lattice cells in the ROI and the transport paths of the at least a portion of simulated particles, a level of each of the lattice cells in the ROI; and
determining, based on the level of each of the lattice cells in the ROI, the evaluation result.

8. The method of claim 7, wherein the adjusting, based on the evaluation result, the particle transport includes;
in response to determining that a simulated particle enters the second lattice cell from the first lattice cell,
splitting, according to a first probability, the simulated particle to generate split simulated particles; and
recording transport paths of the split simulated particles.

9. The method of claim 8, wherein the first probability is equal to a ratio of the first level of the first lattice cell to the second level of the second lattice cell.

10. The method of claim 8, further comprising:
decreasing a weight of each of the split particles relative to the simulated particle such that a total weight of the at least a portion of simulated particles remains unchanged.

11. The method of claim 7, wherein the adjusting, based on the evaluation result, the particle transport includes:
in response to determining that a simulated particle enters the first lattice cell from the second lattice cell,
eliminating, according to a second probability, the simulated particle; and
recording transport paths of simulated particles that are not eliminated in the at least a portion of simulated particles.

12. The method of claim 11, further comprising:
increasing weights of the simulated particles that are not eliminated in the at least a portion of simulated particles such that a total weight of the at least a portion of simulated particles remains unchanged.

13. The method of claim 11, wherein the second probability is equal to a ratio of the level of the second lattice cell to the first level of the first lattice cell.

14. The method of claim 1, wherein
the transport paths of the at least a portion of simulated particles include:
energy information relating to the at least a portion of simulated particles,
speed information relating to the at least a portion of simulated particles, the speed information relates to the at least a portion of simulated
particles including an incident direction of a simulated particle, and path information relating to the at least a portion of simulated particles, and
the obtaining transport paths of at least a portion of simulated particles includes:
designating a recorded transport path of a recorded particle as a transport path of a simulated particle, the recorded particle being identified based on energy information and incident direction information of the recorded particle.

15. The method of claim 14, wherein the path information relating to the at least a portion of simulated particles includes:
type information relating to the at least a portion of simulated particles,
incident position information relating to the at least a portion of simulated particles,
weight information relating to the at least a portion of simulated particles, and
information relating to lattice cells that the at least a portion of simulated particles pass.

16. The method of claim 1, wherein the determining, based on the transport paths, an uncertainty of each of the lattice cells in each of multiple regions of interest (ROIs) includes:
for each of the lattice cells in each of multiple ROIs,
estimating, based on the transport paths, a probability that the at least a portion of simulated particles undergo a reaction in the lattice cell; and determining the uncertainty of the lattice cell based on the estimated probability and an expected probability that the at least a portion of simulated particles undergo the reaction.

17. The method of claim 1, wherein the determining, based on the transport paths, an uncertainty of each of the lattice cells in each of multiple regions of interest (ROIs) includes:
estimating, based on the transport paths, a particle density in each of the lattice cells based on the transport paths;
obtaining a relationship between each of the lattice cells and an expected particle density in each of the lattice cells;
determining, based on the relationship and each of the lattice cells, the expected particle density of each of the lattice cells; and
determining the uncertainty of the lattice cell based on the expected particle density and the particle density.

18. The method of claim 1, further comprising:
obtaining recorded transport paths of simulated particles in one or more lattice cells based on the adjusted particle transport;
determining an energy distribution of the simulated particles in the one or more lattice cells based on the recorded transport paths; and
determining a human dose in radiotherapy based on the determined energy distribution.

19. The method of claim 1, further comprising:
for each of at least one of the lattice cells, performing a dynamic denoising operation on the uncertainty of a lattice cell based on historical transport paths; and
determining the evaluation result associated with the particle transport by evaluating, based on the denoised uncertainty of each of the at least one lattice cell.

20. The method of claim 19, wherein the performing dynamic denoising operation on the uncertainty of a lattice cell includes:
determining a three-dimensional dose distribution of the simulated particles in the lattice cell and an uncertainty corresponding to the three-dimensional dose distribution of the simulated particles in the lattice cell;
performing a filtering operation on the three-dimensional dose distribution such that the filtered three-dimensional dose distribution is differentiable in three dimensions;
determining an uncertainty corresponding to the filtered three-dimensional dose distribution; and
designating the uncertainty corresponding to the filtered three-dimensional dose distribution as the denoised uncertainty of the lattice cell.

* * * * *